US008086295B2

(12) United States Patent
Love et al.

(10) Patent No.: US 8,086,295 B2

(45) Date of Patent: Dec. 27, 2011

(54) COLLAPSIBLE CONTAINMENT WALL FOR IMAGING

(75) Inventors: Alan Love, Chesterland, OH (US); King Li, Highland Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1154 days.

(21) Appl. No.: 11/846,543

(22) Filed: Aug. 29, 2007

(65) Prior Publication Data

US 2008/0081983 A1 Apr. 3, 2008

Related U.S. Application Data

(63) Continuation of application No. PCT/US2007/076973, filed on Aug. 28, 2007.

(60) Provisional application No. 60/827,521, filed on Sep. 29, 2006, provisional application No. 60/895,487, filed on Mar. 19, 2007.

(51) Int. Cl.
*A61B 5/05* (2006.01)
*G01V 3/00* (2006.01)

(52) U.S. Cl. ........................................ 600/407; 324/317

(58) Field of Classification Search ................... 600/407
See application file for complete search history.

(56) References Cited

U.S. PATENT DOCUMENTS

| | | | | |
|---|---|---|---|---|
| 4,979,346 | A * | 12/1990 | Pollard | 52/656.2 |
| 5,080,160 | A * | 1/1992 | Gephart et al. | 160/206 |
| 6,422,571 | B1 * | 7/2002 | Keeney et al. | 277/590 |
| 2001/0010464 | A1 * | 8/2001 | Takamori et al. | 324/304 |
| 2002/0084042 | A1 * | 7/2002 | Kimmet | 160/84.04 |
| 2005/0027189 | A1 * | 2/2005 | Branch et al. | 600/410 |
| 2005/0050800 | A1 * | 3/2005 | Ueda et al. | 49/479.1 |
| 2005/0200360 | A1 * | 9/2005 | Gewiese | 324/318 |
| 2008/0200607 | A1 * | 8/2008 | Ando | 524/588 |

FOREIGN PATENT DOCUMENTS

| | | | |
|---|---|---|---|
| DE | 19639975 | C1 | 5/1998 |
| DE | 10049414 | A1 | 5/2002 |
| DE | 102004007427 | A1 | 9/2005 |
| DE | 102004008343 | A1 | 9/2005 |
| WO | 2007036889 | A2 | 4/2007 |

OTHER PUBLICATIONS

Bell Isolation Systems Products and Services: Isolator Systems http://www.bell-isolation-systems.com/index.asp.

* cited by examiner

*Primary Examiner* — Tse Chen
*Assistant Examiner* — Hien Nguyen

(57) ABSTRACT

A retractable containment wall separates an imaging suite into two sections: a "hot" or contaminated section and a "cold" or non-contaminated section. The wall includes a center portion and retractable peripheral portions. Each retractable portion is made up of several panels. Between panels, between a panel and a room wall, and between a panel and the center portion are tongue and groove seals that mate to form seals at seams in the wall when the wall is deployed. Guide pins propagate along a guide track to facilitate transition of the portions between deployed and retracted orientations. The center portion includes a tube that extends into the imaging region of a diagnostic imaging device located in the non-contaminated portion of the imaging suite. The subject is inserted into the tube in preparation for an imaging procedure.

19 Claims, 7 Drawing Sheets

COLLAPSIBLE CONTAINMENT WALL FOR IMAGING

CROSS REFERENCE TO RELATED APPLICATIONS

This application is a Continuation of PCT/US07/76973 filed Aug. 28, 2007 which claims the benefit of U.S. provisional application Ser. No. 60/827,521 filed Sep. 29, 2006, and U.S. provisional application Ser. No. 60/895,487 filed Mar. 19, 2007, the subject of both of which are incorporated herein by reference.

BACKGROUND

The present application relates to the contamination containment arts. In particular, the application relates to the formation of a parsed imaging suite where one side is contaminated and the other side is uncontaminated through use of a collapsible containment wall and will be described with particular reference thereto.

Few sites, due to cost and overall floor planning, can be developed for the containment of infectious diseases. In the case of an epidemic, such sites cannot handle the desired potential patient capacity, or may not be close enough in location to the center of the epidemic. In such situations, standard hospitals and care centers would be required to accommodate the potential high volume of patients; such institutions, however, are not equipped or prepared to handle such situations. In case there is a rapidly developing biological epidemic, such sites will need to be prepared to form isolated regions in a timely manner.

Concerns about bioterrorism, spread of contagions by air travel, and the like, have increased and are still growing in light of the changes that have occurred in recent years. Threats of biological epidemics are a concern for all parts of the world. While work has commenced in research centers to research vaccines and other ways of treating diseases, there still exists a need of dealing with widespread epidemics.

Medical imaging systems such as magnetic resonance (MR) scanners, gamma cameras, positron emission tomography (PET) scanners, and so forth are advantageously used to examine test subjects in the course of diagnosing and treating infectious diseases. Medical imaging systems, however, are expensive and complex, and they are not readily compatible with an isolated environment. For example, a typical medical imaging instrument includes components that are likely to be damaged by the chemicals or gases typically used in decontamination. Medical imaging instruments also typically include materials and structures that have a high likelihood of trapping and retaining infectious agents such as bacteria, viruses, prions, and so forth. Servicing of medical imaging equipment disposed in isolated environments is also problematic.

In addition to centers that need to be converted into isolation centers to handle biological epidemics, there is also a general need to develop isolation centers that are easier to set up and use, for example, centers that do general research. In such environments, while the biological containment may or may not be life threatening, in all cases it would be desirable to isolate the biological containment from the imaging equipment and the technicians operating and servicing the equipment. In some cases, it is desirable to quickly transition to and from an isolated condition, depending on the nature of the work being conducted.

In the cases mentioned above, or in any other diagnostic imaging setting, there is a need for adapting or reconfiguring imaging suites for different imaging arrangements. Perhaps a larger imaging suite can be divided into smaller suites that temporarily utilize mobile imaging devices. Two adjacent imaging suites could be combined into a single multi-modality suite that temporarily use a common patient support that translates the patient between modalities without rearranging the patient. Other dynamic suite arrangements are certainly feasible as well.

The present application provides a new and improved movable, flexible barrier, which overcomes the above-referenced problems and others.

SUMMARY

In accordance with one aspect, a diagnostic imaging suite is provided. A diagnostic imaging apparatus with an imaging region is disposed in the suite. The suite includes first and second permanent walls. A deployable containment wall, in a deployed configuration, spans a distance between the first and second permanent walls and separates the imaging suite into a potentially contaminated section and a non-contaminated section. The wall hermetically seals the contaminated section from the non-contaminates section.

In accordance with another aspect, a method of creating an isolated imaging environment by constructing a wall is provided. A plurality of panels are extended along a guide track from a permanent wall to a center portion. A junction between the panels and the permanent wall is sealed. A junction between the panels and the center portion is sealed. Junctions between panels are sealed. Then, junctions between the panels and the guide track are sealed.

In accordance with another aspect, a deployable containment wall for isolating a hot side of an imaging suite from a clean side is provided. A center portion is mounted adjacent an imaging apparatus with an aperture aligned with a patient receiving region of the imaging apparatus. A containment tube is removably connected with the center portion surrounding a patient receiving imaging region of the imaging apparatus. A plurality of deployable panels are hingedly connected with each other and are configured to be movably received in tracks extending along a ceiling and a floor of the imaging suite, such that the panels are movable between a deployed configuration extending between walls of the suite and the center portion and a retracted configuration. Seals seal junctions between the deployable panels, the deployable panels and the center portion, the deployable panels and the permanent walls, the deployable panels and the floor and ceiling, and the containment tube and the center portion such that the contaminated section of the suite is isolated from the non-contaminated side.

One advantage lies in providing isolated medical imaging capabilities.

Another advantage lies in conversion of a non-isolated imaging suite to an isolated imaging suite.

Another advantage lies in upgradeability of imaging suites to have isolation capabilities.

Still further advantages of the present invention will be appreciated to those of ordinary skill in the art upon reading and understand the following detailed description.

DRAWINGS

The invention may take form in various components and arrangements of components, and in various steps and arrangements of steps. The drawings are only for purposes of illustrating the preferred embodiments and are not to be construed as limiting the invention.

DESCRIPTION

Figure 1:
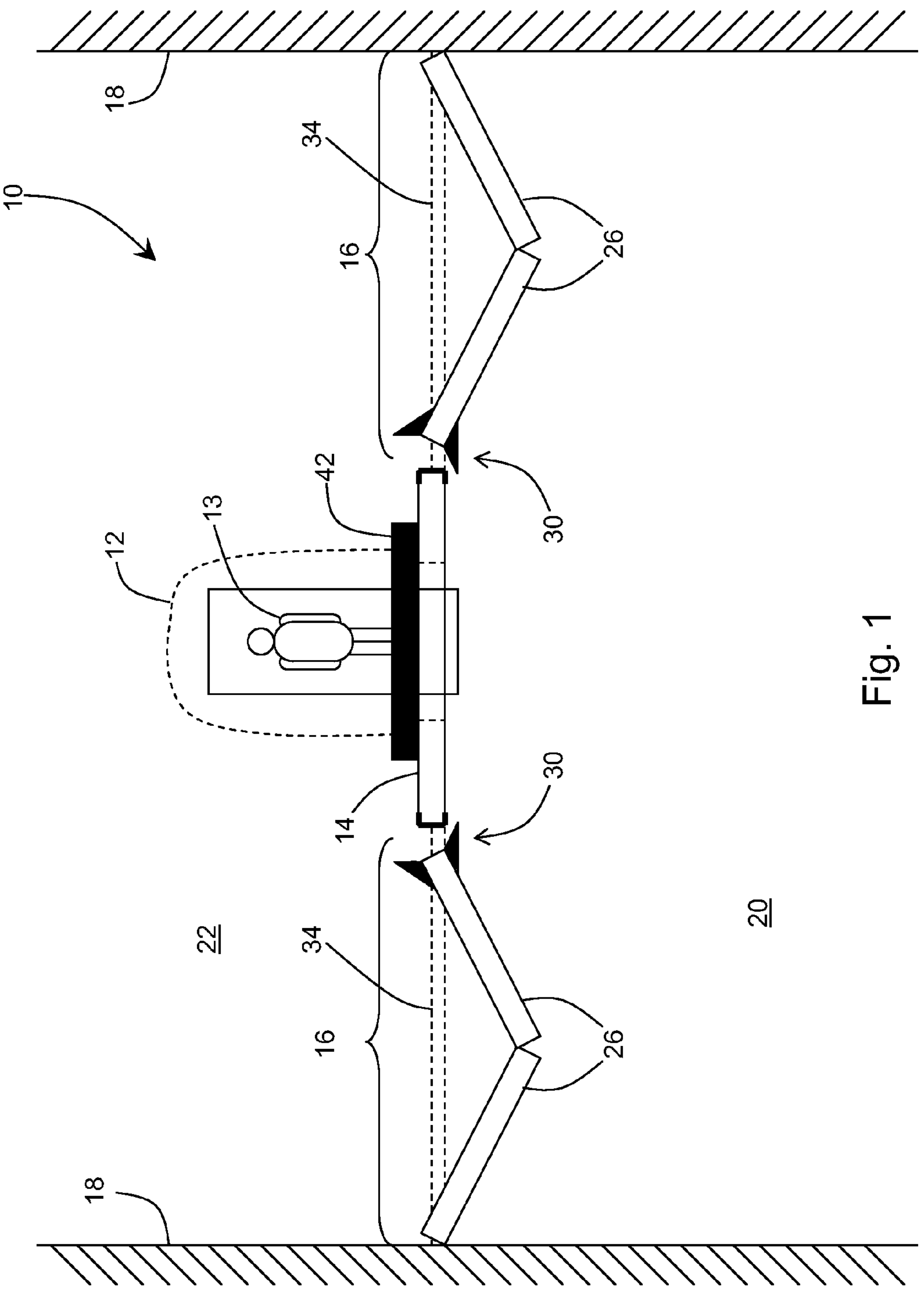
FIG. 1 is a top-down view of an extendable wall in accordance with the present application.

With reference to FIG. 1, a collapsible containment wall 10 can be deployed to establish an isolated imaging region. In such applications, the wall 10 would isolate a patient handling and loading side from an imaging side, in which the imaging equipment and imaging technicians reside. A containment tube 12 passes through the containment wall 10, wherein a patient 13 can be transported through the wall and into the imaging region for imaging by the imaging equipment. The containment tube 12 maintains the isolation between the patient 13 on the loading side and the imaging equipment on the imaging side.

Figure 2:
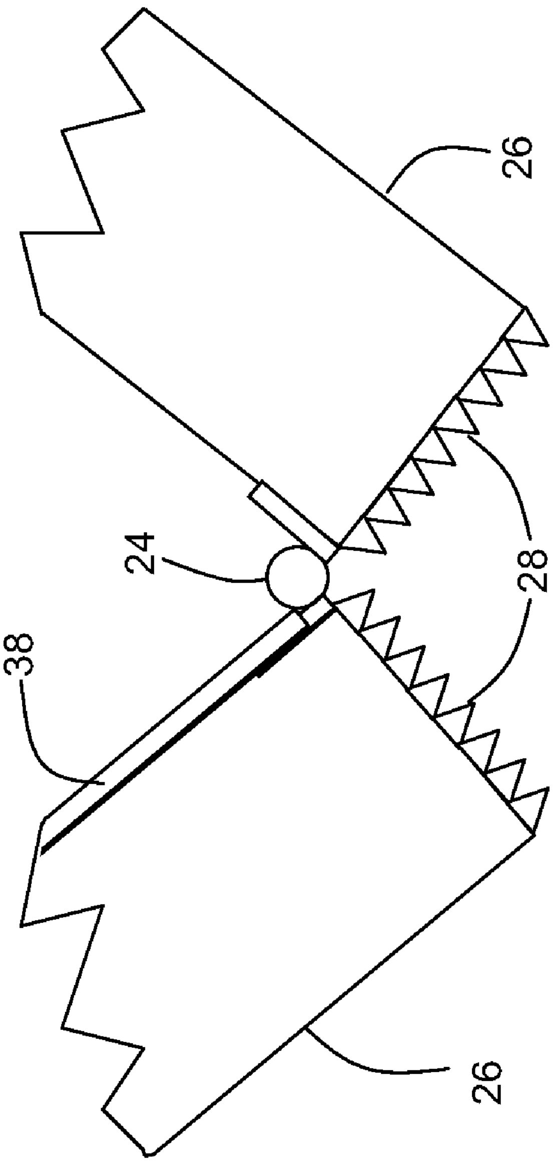
FIG. 2 is a detailed view of the junction of two wall segments of the wall of FIG. 1.
Figure 3:
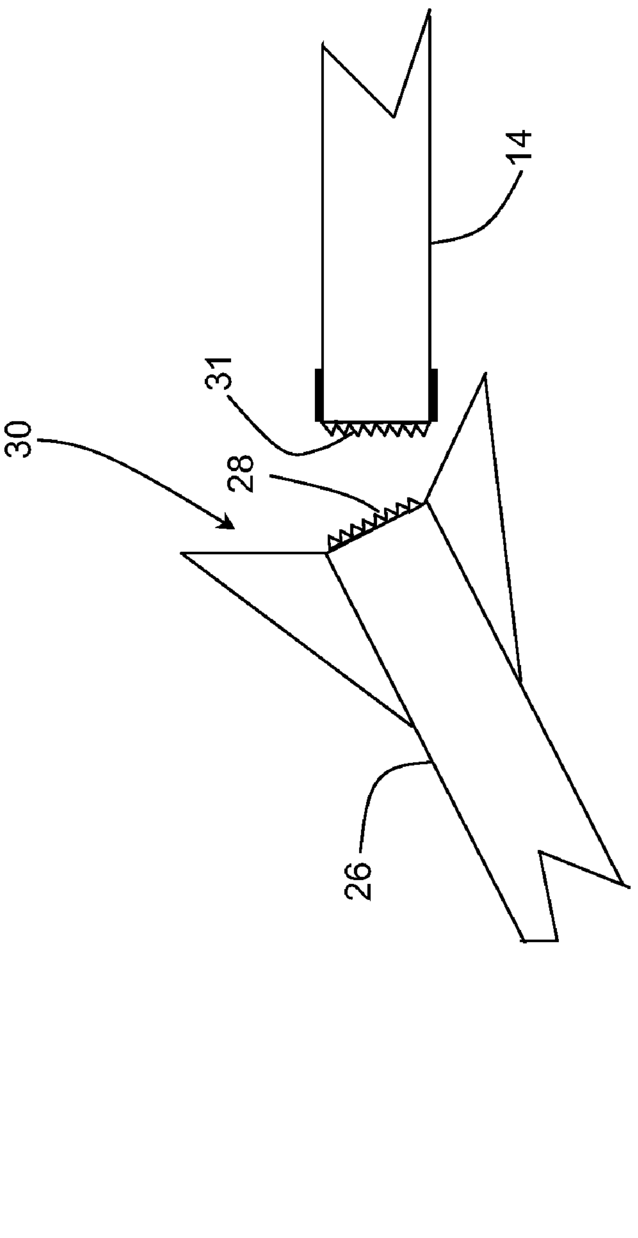
FIG. 3 is a detailed view of the junction between a wall segment and a center wall segment of the wall of FIG. 1.
Figure 4:
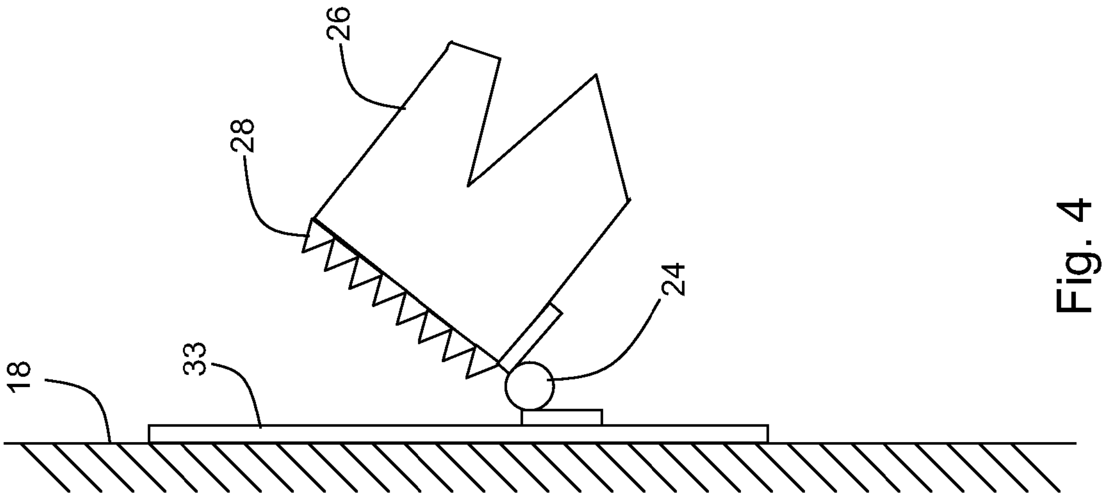
FIG. 4 is a detailed view of the junction between a wall segment of the wall of FIG. 1 and a fixed room wall.

The illustrative embodiment shown in FIG. 1 includes a fixed center panel 14 and two folding or collapsible wall portions 16. In such an embodiment, when an isolated imaging suite is to be established, the two end portions 16 fold out from the room walls 18 and seal to the fixed center wall 14. When fully extended, the wall portions 16 define a “hot side” 20 that is contaminated and quarantined, i.e., the loading side, and a “cold side” 22 that is uncontaminated, i.e., the imaging side. FIGS. 2, 3, and 4 illustrate exemplary hinges and ends that attach to form seals.

With reference to FIG. 2 a “piano hinge” 24 holds two panels 26 of the wall portion 16 together. While only two wall panels 26 are shown to form a wall portion 16, it is to be understood that more panels can be connected depending on the size of the panels 26, size of the imaging suite, and the like. The wall panels 26 are preferably non-permeable plastic, and resistant to decontamination chemicals typically used in a containment or decontamination. Exemplary material for construction of the panels 26 includes cyclic olefin copolymer (COC) plastic. The panels 26 are thick enough to resist breaking from normal use, but thin enough to establish a balance between breakable and cumbersome. Preferably, the wall panels 26 are about ⅜ thick. The wall panels 26 can be clear, translucent, or opaque. The hinge 24 also allows the wall portion 16 to be folded at the hinge 24. On the ends of the wall panels 26, where one wall panel 26 meets another, there is a multiple tongue and groove mating seal 28. The seal 28 is preferably constructed of high durameter sealing rubber. When the wall panels 26 are extended, the “teeth” of the seal 28 intermesh to create a containment seal between panels 26.

With reference now to FIG. 3, a clamping assembly 30 between the movable panels 26, and the fixed wall 14, includes the multiple tongue and groove seal 28 which mates with a similar tongue and groove section 31 on the end of the center wall 14.

With reference now to FIG. 4, another “piano hinge” type hinge 24 is connected with an end of the collapsible wall portion 16 where it attaches to the existing room walls 18. The end of the wall portion 16 adjacent the room wall also has the tongue and groove seal 28 that mate with a rubber sealing sheet 33 mounted to the room wall 18. It should be appreciated that other types of hinges can be used to allow the wall 10 to fold, and form a sealed wall when deployed. The hinges 24 may include one or more gaskets to ensure an airtight seal. In addition, a foam or liquid sealant may be applied to the hinge to further ensure an airtight seal.

Figure 5:
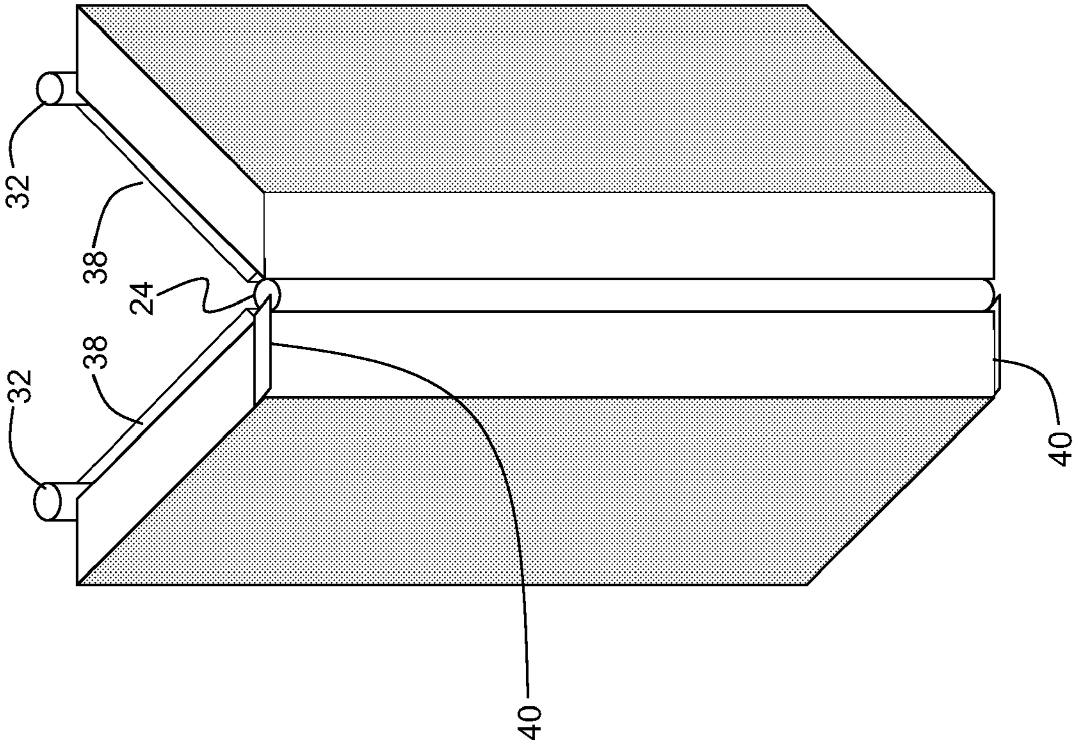
FIG. 5 is a perspective view of a wall portion of the wall of FIG. 1.
Figure 6:
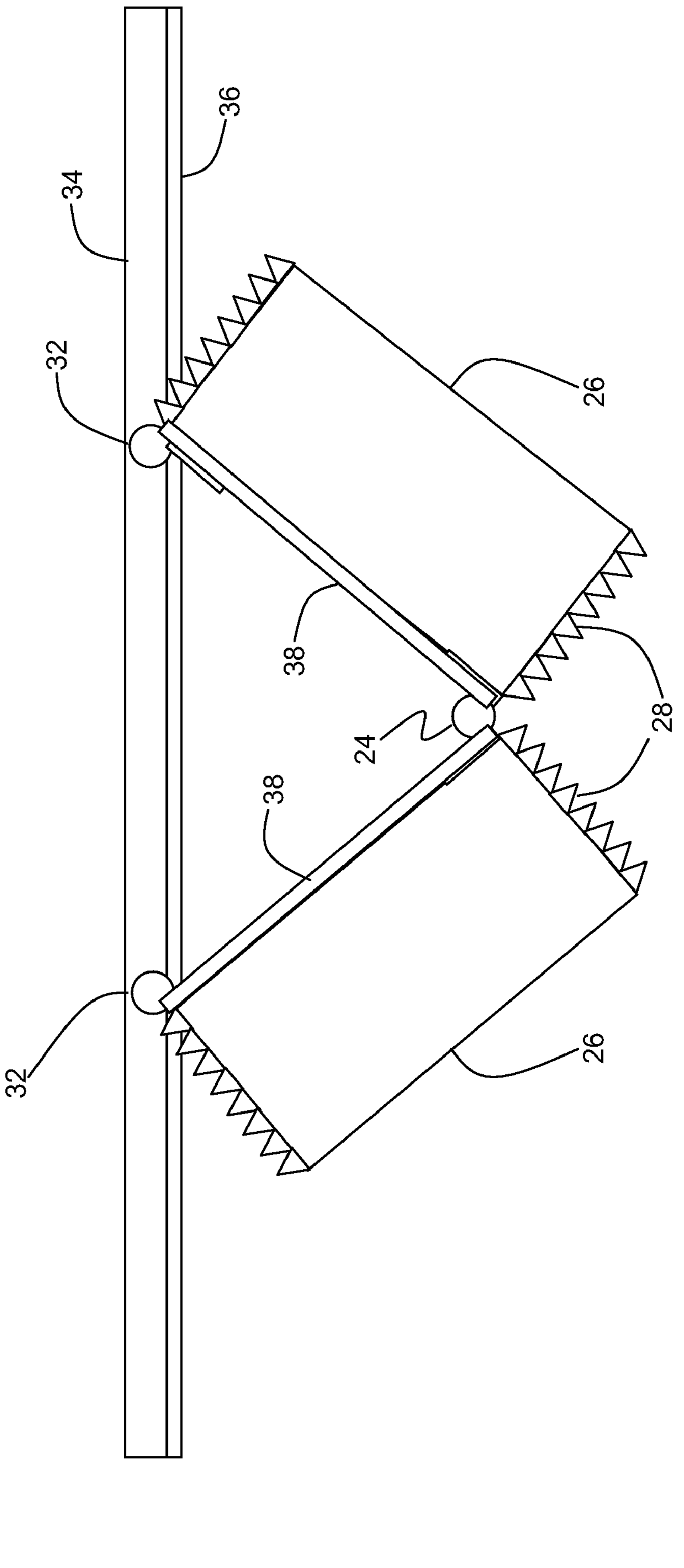
FIG. 6 is a top-down view of two wall segments of the wall of FIG. 1 engaging a guide track.

With reference now to FIGS. 5 and 6, on one end of a panel 26, there is a combined hinge/guide track pin assembly 32. The hinge/pin 32 has an extended end that is received in a guide track 34 on both the floor and the ceiling of the imaging suite. The guide track 34 allows the wall 10 to be quickly deployed while ensuring sufficient mating of the various seals. The guide track 34 provides a tight tolerance path for the panels 26 to open and close and enable satisfactory sealing when the wall 10 is deployed. The edge of the guide track 34 on the side adjacent the wall panels 26 is fitted with a rubber sealing sheet 36 so that the top and bottom of the wall 10 is also sealed when the wall 10 is deployed. The guide track sheet 36 preferably mates with edge sealing sheets 38 that run along the top and bottom edges of the wall segments 26. The teeth of these sheets run in rows parallel to the floor, that is, effectively 90° with respect to the direction of the teeth on the edges of the panels. At the junction of adjacent panels 26, a wing 40 extends from the top (or bottom) edge of one panel 26 over the edge of the adjacent panel 26. The wing 40 provides a complete seal at the joint of the top and bottom edges of the panels 26. This feature is best visualized in FIG. 5 (not shown in FIG. 6). The top and bottom of the wall could also include a gasket or other feature to ensure a seal between the containment wall 10 and the ceiling and floor, respectively, of the existing room.

The fixed center wall 14 can be in place during normal imaging conditions. The fixed center wall 14 is relatively thin and minimally intrusive to standard imaging procedures. The patient 13 would merely pass through a corresponding aperture in the center wall 14 prior to entering the imaging region. Further, the fixed center wall 14 can be decorated or include other features to make it aesthetically pleasing.

In situations that call for an isolated imaging suite, the detachable containment tube 12 can be quickly attached to a flange 42 located on the fixed center wall. The junction between the flange 42 and the containment tube 12 includes tongue and groove sealant surfaces that are similar to the seals 28 between panels 26. The wall ends 16 can then be extended from a folded configuration adjacent the room walls 18 and abuttingly sealed to the fixed center wall 14 and each other. In this way, isolation between the hot and cold sides 20, 22 of the imaging suite is established. When the isolated conditions are not required, however, the tube 12 can be removed from the center wall portion 14 and set aside, and the panels 26 can be retracted.

It should be appreciated that the center wall portion 14 does not need to be fixed. It may fold out away from the walls 18 like the other panels 26 or be fixed in place with removable pins, clamps, etc. In such situations, the opening in the containment wall 10 to which the containment tube 12 is attached should be aligned isocentrically with the center of an imaging region of the imaging device. Thus, while a fixed wall 14 ensures alignment of the opening, and hence the tube 12, alternative registration mechanisms can be put in place to ensure proper alignment of the tube 12. It should also be appreciated that exact alignment may not be required, but it is preferred. The wall 10 also does not need to fold out away from the existing walls 18, but instead may come down from the ceiling, up from the floor, include panels that are manually set into place, or any combination thereof. Still even other ways of collapsing the wall 10 can be used. For example, the wall 10 may be one piece, wherein the center is positioned by a set of pins or other registration mechanism and the ends of the wall 10 can then extend or fold out to attach to the existing sidewalls 18. It should further be appreciated that all such methods of collapsing the containment wall 10 are merely illustrative and that one skilled in the art should understand and appreciate that other methods of collapsing and extending the walls may exist.

Figure 7:
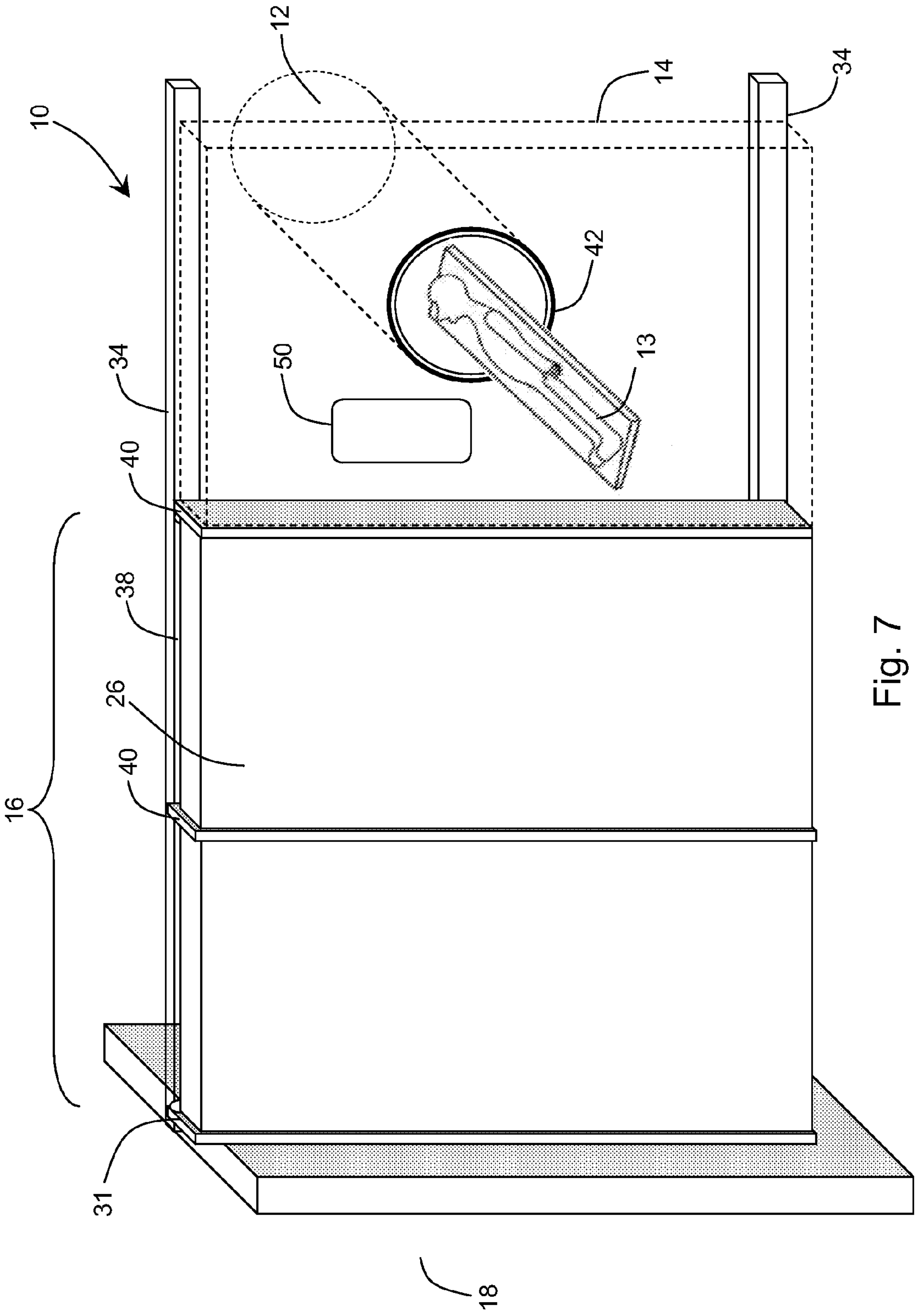
FIG. 7 is a perspective view of a portion of the wall of FIG. 1 in a deployed orientation.

With reference now to FIG. 7, the containment wall 10 is shown in a deployed, that is, a sealed orientation. Adjacent the patient tube 12 in the fixed panel 14, there is a patch panel 50. The patch panel 50 provides an electronic interface between the contaminated portion 20 and the non-contaminated portion 22 should there be a need to have imaging equipment (such as a local receive coil in a magnetic resonance imaging setting) on the hot or contaminated side. Cables from the device link to the patch panel 50 and then (on the non-contaminated side) connect to the rest of the imaging apparatus, post imaging processors, or the like.

As can be appreciated, the containment wall 10 can be quickly moved into place whenever isolation is desired, and then removed when a more standard imaging environment is desired. It should be appreciated that the material used for the containment wall 10 should be resistant to decontamination materials. In some embodiments, the wall includes rigid or semi-rigid panels, while in other embodiments the wall or portions of the wall can be formed by a sheath or other flexible material. In some embodiments, the wall or portions of the wall can be disposed after decontamination and replaced with a new containment wall or wall panels.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A diagnostic imaging suite comprising:

a diagnostic imaging apparatus with an imaging region;

a ceiling and a floor;

first and second permanent walls;

a deployable containment wall that, (1) in a deployed configuration, spans a space between the first and second permanent walls, separating the imaging suite into a potentially contaminated section and a non-contaminated section, the wall sealing the contaminated section from the non-contaminated section, and (2) in a retracted configuration, the wall retracts to open the space between the first and second permanent walls providing open access between the contaminated section and the non-contaminated section, the deployable wall including:

a panel having an aperture, and a plurality of foldable panels;

a containment tube configured to be mounted to the panel having the aperture and extending into the imaging region; and seals which seal between the panels, between the panels and the ceiling, the floor and the first and second permanent walls, and between the containment tube and the panel having the aperture.

2. The diagnostic imaging suite as set forth in claim 1, wherein at least a portion of the imaging apparatus that defines the imaging region is present in the non-contaminated section while a subject to be imaged is entirely present in the contaminated section of the imaging suite.

3. The diagnostic imaging suite as set forth in claim 1, wherein the panel having the aperture includes a flange to which the containment tube is removably attached.

4. The diagnostic imaging suite as set forth in claim 1, wherein the foldable panels include an edge sealing structure for sealing a juncture between the panels and a guide track.

5. The diagnostic imaging suite as set forth in claim 4, wherein the guide track includes a guide track sealing structure that engages the edge sealing structure of the panels for facilitating sealing of the juncture between the panels and at least one of the guide track and a floor.

6. The diagnostic imaging suite as set forth in claim 1, where at least one of the panels includes wings for sealing junctures between panels at the floor and the ceiling.

7. The diagnostic imaging suite as set forth in claim 1, wherein the panel having the aperture includes a patch panel that provides an electronic interface between the contaminated section and the non-contaminated section.

8. A diagnostic imaging suite comprising:

a diagnostic imaging apparatus with an imaging region;

first and second permanent walls;

a deployable containment wall that, in a deployed configuration, spans a distance between the first and second permanent walls separating the imaging suite into a potentially contaminated section and non-contaminated section, the wall sealing the contaminated section from the non-contaminated section, wherein the deployable wall includes:

a center portion mounted adjacent the imaging apparatus;

an aperture in the center portion for receiving a containment tube that is removably connected with the center portion to surround a patient receiving imaging region of the imaging apparatus;

tracks extending along at least one of a ceiling and a floor from at least the center portion to the permanent walls;

a plurality of deployable panels hingedly connected with each other and being movably received in the tracks to move between a retracted configuration and a deployed configuration in which the panels extend from each permanent wall to the center section; and seals which seal between the deployable panels, between the deployable panels and the center portion, between the deployable panels and the permanent walls, between the deployable panels and the floor and ceiling, and between the containment tube and the center portion such that the contaminated section of the suite is isolated from the non-contaminated side.

9. The diagnostic imaging suite as set forth in claim 8, wherein at least some of the seals include a plurality of alternating and mating tongues and grooves.

10. A method of creating an isolated imaging environment comprising:

extending a plurality of panels from a permanent wall of an imaging suite along ceiling and floor guide tracks;

disposing a containment tube into an imaging region of a diagnostic imaging apparatus;

attaching the containment tube to a flange around an aperture in one of the panels;

sealing a junction between the containment tube and the flange;

sealing a junction between the panels and the permanent wall;

sealing junctions between the panels;

sealing a junction between the panels and the ceiling and floor guide tracks such that the imaging suite is divided into biocontaminant isolated sides.

11. The method as set forth in claim 10, wherein the steps of sealing include engaging tongue and groove seals with each other.

12. An apparatus that performs the steps of claim 10.

13. The method as set forth in claim 10, wherein extending the panels and sealing the junctions separates an imaging suite into a potentially contaminated section and a non-contaminated section which are separated and sealed from each other and further including:

retracting the plurality of panels to provide open communication between the potentially contaminated and non-contaminated sections.

14. The method as set forth in claim 13, wherein the panels are extended and retracted along a guide track.

15. The method as set forth in claim 10, further including:

after imaging a subject, biodecontaminating at least one side of the imaging;

biodecontaminating and removing the containment tube;

selectively retracting the containment wall so that walking access is provided between the biodecontaminated side and a non-contaminated portion of the imaging suite when the suite is reconfigured to a state of non-biocontainment.

16. A deployable containment wall for isolating a hot side of an imaging suite from a clean side, the wall comprising:

a plurality of deployable panels hingedly connected with each other and being configured to be movably received in tracks extending along a ceiling and a floor of the imaging suite, such that the panels are movable between a deployed configuration extending between permanent walls of the suite to separate the hot side and the clean side and a retracted configuration to connect the hot side and the clean side;

a center wall panel mountable adjacent an imaging apparatus and defining an aperture aligned with a patient receiving region of the imaging apparatus;

a containment tube surrounding the patient receiving imaging region of the imaging apparatus, in the deployed configuration, the containment tube is sealed to the center wall panel around the aperture;

seals which in the deployed configuration seal between the deployable panels, between the deployable panels and the center wall panel, between the deployable panels and the permanent walls, and between the deployable panels and a floor and ceiling of the imaging suite, such that the hot side of the imaging suite is isolated from the clean side.

17. The deployable containment wall as set forth in claim 16, wherein at least some of the seals include a plurality of alternating and mating tongues and grooves.

18. The deployable containment wall as set forth in claim 16, further including:

at least one gasket and liquid sealant are disposed adjacent to a hinge connection of the a plurality of deployable panels.

19. An imaging suite having a deployable wall which is deployed to divide the imaging suite into separated first and second sections and retractable to unite the sections of the imaging suite to a single space in a retracted configuration, the deployable wall comprising:

tracks extending between the first and second sections;

a plurality of panels movably received in the tracks such that in the deployed configuration the panels are disposed end to end between opposite permanent walls of the imaging suite and in the retracted configuration are disposed adjacent the permanent walls, one of the panels having an aperture therein;

a containment tube which is connected with the panel which has the aperture in alignment with the aperture to extend in the deployed configuration into an imaging region of a diagnostic imaging apparatus, such that in the deployed configuration a patient on one side of the deployable wall can be positioned in the imaging region of the diagnostic scanner on an opposite side of the wall by positioning the patient in the containment tube; and seals configured to seal between the deployable panels, between the panels and the permanent walls between the panels and the tracks and between the containment tube and the panel which has the aperture.

* * * * *